US011589994B2

(12) United States Patent
Smith et al.

(10) Patent No.: US 11,589,994 B2
(45) Date of Patent: Feb. 28, 2023

(54) AUGMENTS, SYSTEMS AND METHODS FOR ACETABULAR IMPLANTS

(71) Applicant: Biomet Manufacturing, LLC, Warsaw, IN (US)

(72) Inventors: Aaron P. Smith, Warsaw, IN (US); Stephanie Klunk, Hamilton, OH (US); Kirk J. Bailey, Rochester, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 289 days.

(21) Appl. No.: 16/315,097

(22) PCT Filed: Jul. 7, 2017

(86) PCT No.: PCT/US2017/041115
§ 371 (c)(1),
(2) Date: Jan. 3, 2019

(87) PCT Pub. No.: WO2018/009807
PCT Pub. Date: Jan. 11, 2018

(65) Prior Publication Data
US 2019/0209329 A1    Jul. 11, 2019

Related U.S. Application Data

(60) Provisional application No. 62/360,136, filed on Jul. 8, 2016.

(51) Int. Cl.
*A61F 2/34* (2006.01)
*A61F 2/30* (2006.01)
(Continued)

(52) U.S. Cl.
CPC ...... *A61F 2/30734* (2013.01); *A61F 2/30749* (2013.01); *A61F 2/34* (2013.01);
(Continued)

(58) Field of Classification Search
CPC .................. A61F 2002/3432; A61B 17/8066
See application file for complete search history.

(56) References Cited

U.S. PATENT DOCUMENTS 5,282,861 A    2/1994  Kaplan
5,314,490 A *  5/1994  Wagner ............... A61F 2/34
                                                      623/22.36
(Continued)

FOREIGN PATENT DOCUMENTS

WO    WO-9922672 A2    5/1999
WO    WO-02083035 A2   10/2002
(Continued)

OTHER PUBLICATIONS

Translation of WO 02/083035 A2 retrieved from Espaceneton Aug. 3, 2021 (Year: 2021).*
(Continued)

*Primary Examiner* — Megan Y Wolf
(74) *Attorney, Agent, or Firm* — Schwegman Lundberg & Woessner, P.A.

(57) ABSTRACT

The augments, systems and methods for supporting acetabular implants described herein can include an augment (100) for supporting an acetabular shell (90) having a first portion (136) of a locking mechanism. The system can also include a shell having a second portion of a locking mechanism (96). The first portion of the locking mechanism and the second portion of the locking mechanism can be adapted to move relative to one another from an unlocked state to a locked state to fixedly couple the augment to the shell. In some examples, the augment can be contourable to match the shape of a bone.

15 Claims, 10 Drawing Sheets

(51) Int. Cl.
*A61F 2/46* (2006.01)
*A61B 17/88* (2006.01)

(52) U.S. Cl.
CPC ........ *A61F 2/4609* (2013.01); *A61B 17/8863* (2013.01); *A61F 2002/30331* (2013.01); *A61F 2002/30383* (2013.01); *A61F 2002/30387* (2013.01); *A61F 2002/30507* (2013.01); *A61F 2002/30522* (2013.01); *A61F 2002/30578* (2013.01); *A61F 2002/30579* (2013.01); *A61F 2002/30604* (2013.01); *A61F 2002/30736* (2013.01)

(56) References Cited

U.S. PATENT DOCUMENTS

| | | | | |
|---|---|---|---|---|
| 5,336,224 | A | * | 8/1994 | Selman .............. A61B 17/8085 606/280 |
| 6,306,173 | B1 | * | 10/2001 | Masini .............. A61B 17/8066 623/22.32 |
| 6,454,809 | B1 | * | 9/2002 | Tornier .............. A61F 2/30734 623/22.32 |
| 8,556,986 | B2 | | 10/2013 | Haidukewych |
| 2005/0288793 | A1 | * | 12/2005 | Dong .................. A61F 2/34 623/22.28 |
| 2008/0021568 | A1 | | 1/2008 | Tulkis et al. |
| 2013/0035766 | A1 | | 2/2013 | Meridew |
| 2013/0184832 | A1 | | 7/2013 | Haidukewych |
| 2013/0304067 | A1 | * | 11/2013 | Hess .................. A61B 17/8004 606/71 |

FOREIGN PATENT DOCUMENTS

| | | |
|---|---|---|
| WO | WO-2011156504 A2 | 12/2011 |
| WO | WO-2018009807 A1 | 1/2018 |

OTHER PUBLICATIONS

"International Application Serial No. PCT/US2017/041115, International Search Report dated Nov. 29, 2017", 9 pgs.
"International Application Serial No. PCT/US2017/041115, Invitation to Pay Additional Fees and Partial Search Report dated Oct. 6, 2017", 14 pgs.
"International Application Serial No. PCT/US2017/041115, Written Opinion dated Nov. 29, 2017", 9 pgs.
Levine, Brett R. et al., "Experimental and clinical performance of porous tantalum in orthopedic surgery", Biomaterials, (27), (Sep. 2006), 4671-81.
"European Application Serial No. 17740263.3, Response to Communication pursuant to Rules 161(1) and 162 EPC filed Sep. 17, 2019", 22 pages.
"European Application Serial No. 17740263.3, Communication pursuant to Article 94(3) EPC dated Mar. 19, 2020", 4 pages.

* cited by examiner

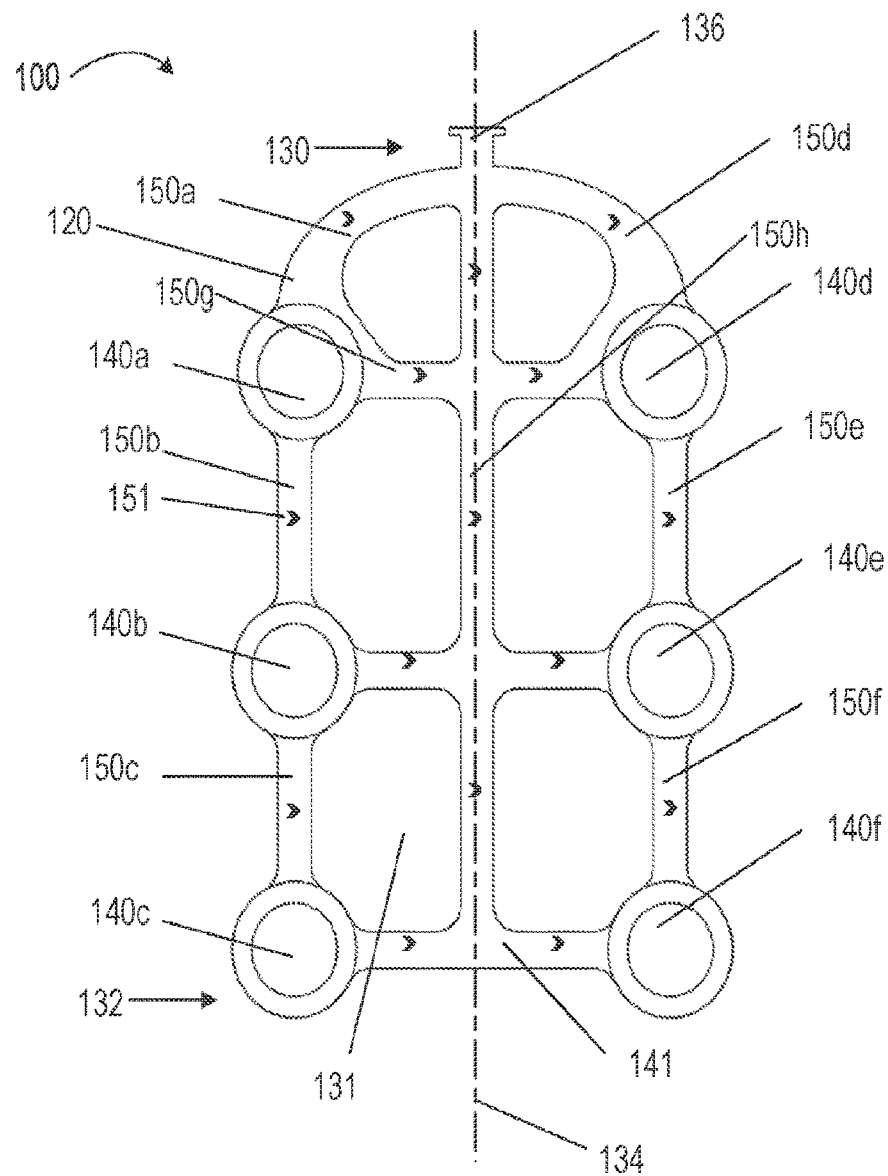

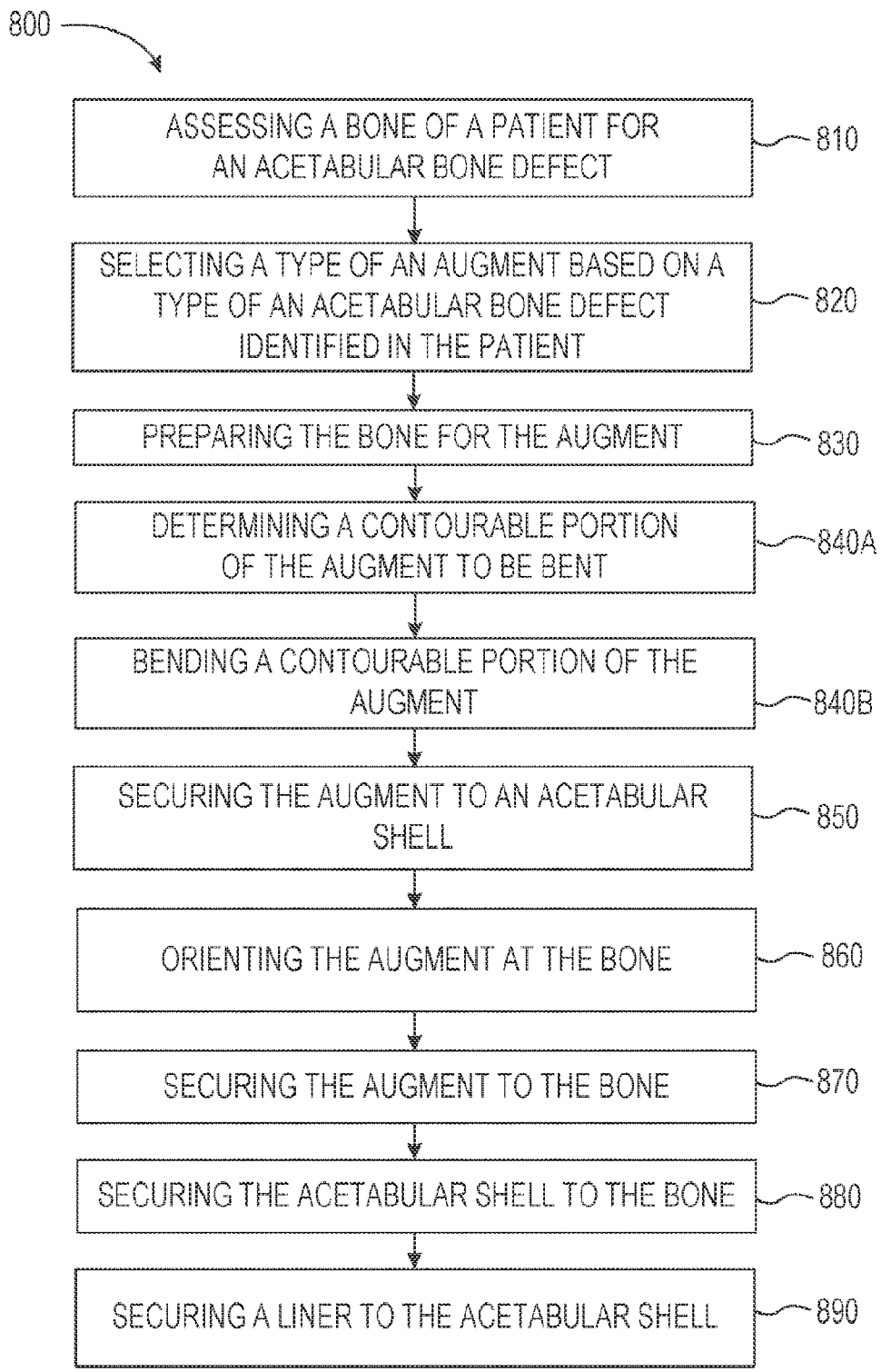

AUGMENTS, SYSTEMS AND METHODS FOR ACETABULAR IMPLANTS

CLAIM OF PRIORITY

This application is a U.S. National Stage Application under 35 U.S.C. 371 from International Application Serial No. PCT/US2017/041115, filed on Jul. 7, 2017, and published as WO 2018/009807 A1 on Jan. 11, 2018, which claims the benefit of U.S. Provisional Patent Application Ser. No. 62/360,136, filed on Jul. 8, 2016, the benefit of priority of each of which is claimed hereby, and each of which is incorporated by reference herein in its entirety.

TECHNICAL FIELD

This document pertains generally, but not by way of limitation, to orthopedic devices, and, more particularly, augments that support acetabular implants used in total hip arthroplasty.

BACKGROUND

A total hip arthroplasty (THA) procedure can be performed to repair a diseased or damaged hip joint and replace it with a hip prosthesis. Sometimes, as with any other mechanical device, a total hip replacement can be subject to various forms of mechanical or biological issues. When issues occur, a reoperation of the hip prosthesis can be necessary to resolve the issues. Such a reoperation of a THA is called a revision THA. This is usually done several years after the original implantation and is more common in patients who had the initial THA performed at a young age and the patient chose to have a very active physical lifestyle.

One of the challenges of a THA, including a revision THA is how to securely implant the hip prosthesis. In particular, it can be challenging to securely implant and support an acetabular shell of the prosthesis into the remaining bone of the patient, especially in the presence of poor bone quality or bone loss. In addition, it can be challenging when using an augment to support an acetabular shell, to have a secure coupling of the augment to the acetabular shell.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

FIG. 1A is a top view of an illustrative augment, in accordance with at least one example.

FIG. 8 is a flow chart illustrating a method of using augments to secure an acetabular shell to a bone of a patient, in accordance with at least one example.

DETAILED DESCRIPTION

Figure 1B:
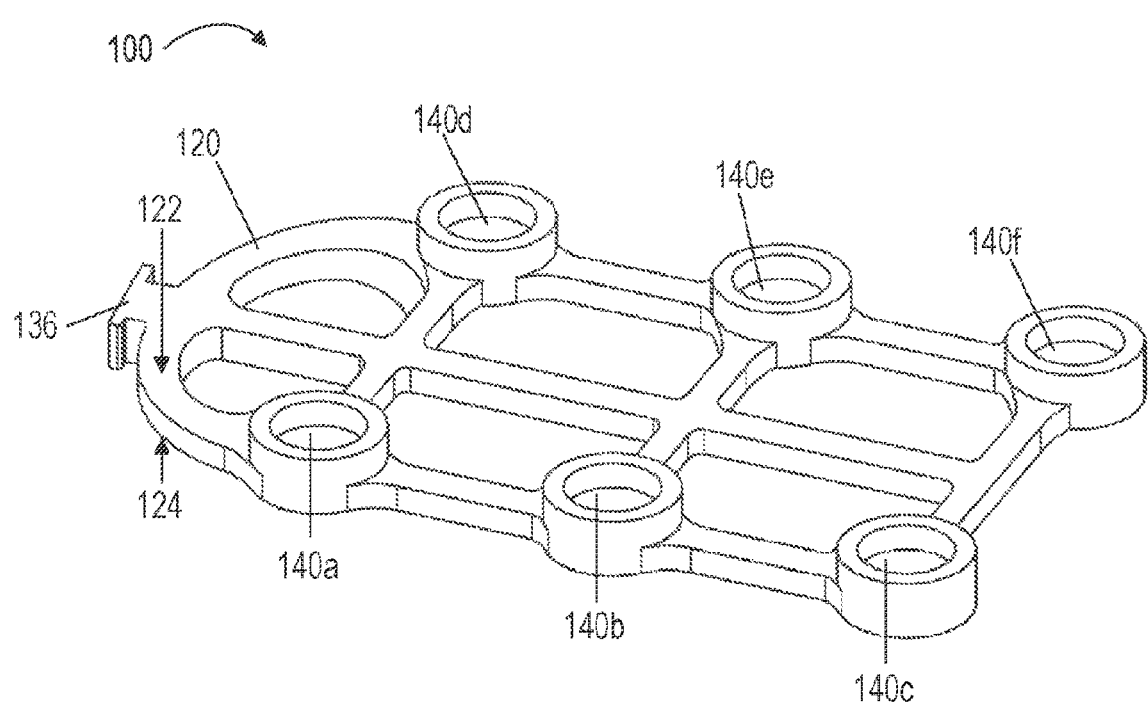
FIG. 1B is a side perspective view of the illustrative augment of FIG. 1A, in accordance with at least one example.

As discussed above, one of the challenges of a total hip arthroplasty (THA), including a revision THA, is how to securely implant the hip prosthesis. In particular, it can be difficult to implant an acetabular revision shell of the prosthesis into the remaining bone of the patient, especially in the presence of poor bone quality or bone loss. In addition, it can be challenging when using an augment to support an acetabular shell, to establish and maintain a secure coupling of the augment to the acetabular shell.

When using conventional acetabular revision shells, surgeons can employ the use of additional augments to reinforce the attachment of the shell to the bone and to secure the augment to the shell. Additional components can include a cup-cage construct for example. Cup-cage constructs can be used to provide a secure attachment of the shell (e.g., cup) to the bone when the surgeon determines there is a risk of the shell migrating or loosening. The cage holds the acetabular shell in place long enough to provide biological fixation to the acetabular shell. However, the cup-cage construct reduces an allowable head size that can be placed in the shell.

In addition, surgeons are limited to off the shelf options having specified dimensions. These off the shelf augments limit the surgeon's ability to match the implant to the specific needs and dimensions of the patient. The surgeon, selecting from these off the shelf options, is limited in finding a best match for fixing the shell to the available bone. When the augments are too large or too small and the surgeon tries to match the augments up with the available bone, it does not always produce the desired results. An augment having a contour that is different than the contour of the bone may not provide the desired fixation of the implant to the bone. In this situation, the augment can interfere with the patient's anatomy adjacent the implant site including bone, muscle, tendon or ligament tissues.

The other option available to surgeons is to have a patient specific, fully customized implant manufactured. This option also has issues. Fully customized implants are not readily available off the shelf. They are manufactured to match a particular patient based on imaging data for the particular patient.

The augments, systems and methods disclosed herein can improve surgeon options for attaching acetabular shells to an acetabulum of patient in a more customizable manner, and without the expense of a fully customized, patient-specific implant. Because the augments are more customizable to the patient over conventional augments, the quality of the implantation can be made more reliable.

To provide a secure attachment between the augment and the shell, the augment and the shell can be cemented or fastened together, such as by a fastener. These both require additional components or materials, and extra steps, and can result in as strong of a coupling as is desired.

To address these issues, improved augments and methods for supporting acetabular shells are described herein. The augments and methods can include modification options to increase the customizability of the augments to better match the anatomy of a patient. The augments have been found by the inventors to solve the problem of providing sufficient screw fixation in revision total hip arthroplasty (THA) when many fasteners can be required to achieve biological fixation of the shell, while providing the ability to change the contour of portions of the augment. The augments and methods can allow tailored fixation of the augment to the particular patient. In other words, the improved augments can provide individualized customization to the particular patient's anatomy in an "off the shelf" design. The advantages of the improved augments can include, for example: providing flexibility to the surgeon to contour an "off the shelf" implant to match the native bone.

This disclosure also includes improved acetabular shell and augment systems including attachments and attachment methods that provide a locking mechanism between the augment and the acetabular shell. The systems, augments and acetabular shells preserve a maximized head size within the cup because the use of a cage can be eliminated by the improved attachments and methods.

Another feature of an improved augment can include having a smooth surface on specified portions of the augment, and having a porous surface that promotes boney ingrowth on other specified portions of the augment. The advantages of such a surface arrangement can include facilitating improved attachment to the bone along the porous surface portions, while the smooth surface portions can be arranged to reduce irritation of adjacent tissue, including adjacent muscle tissue that covers the hip bone.

The disclosure herein while applied to implanting shells, can also be applied to implanting cups, such as a cup inserted into a shell that acts as a liner, or a cup that is directly implanted without a shell. In addition, while the augments and methods can be described in relation to revision THA, the augments and methods can also be applied to non-revision, or first time THA surgeries and prosthesis.

As described herein, the term "opening" or "hole" is generally associated with a screw hole, but it is not limited to holes that can only be used with screws. Other suitable types of fasteners besides screws can be inserted through the holes disclosed herein.

FIG. 1A is a top view and FIG. 1B a side perspective view of an illustrative augment 100 for supporting an acetabular shell (e.g., FIG. 2A, 90) at a hip bone, in accordance with at least one example. As a general overview, the example augment 100 can include contourable portions 150a-h to allow customization of the augment 100 to fit a particular patient's anatomy. The augment 100 can also include a first portion 136 of a locking mechanism to create a locked state (e.g., FIGS. 2A, 2B and 3) between the augment 100 and an acetabular shell (e.g., FIG. 2A, 90).

As shown in FIG. 1B, the augment 100 can include a body 120 having a first surface 122 and a second surface 124 opposite the first surface 122. As shown in FIG. 1A, the body 120 can extend from a first end portion 130 to a second end portion 132. In some examples the body 120 can be described as extending in a direction, such as along a longitudinal axis 134 from the first end portion 130 to the second end portion 132 (FIG. 1A). The provision of the longitudinal axis 134 does not necessarily mean that the augment 100 extends symmetrically along the longitudinal axis 134 or is aligned with the longitudinal axis 134, although in some examples, it can be. Rather, the longitudinal axis 134 is provided as a general directional relationship of the augment 100 to itself and, in some examples, to an acetabular shell (e.g., FIG. 2A, 90) that it can be adapted to be attached to. Furthermore, any other features that are described as extending along the longitudinal axis 134 are also not necessarily aligned with, parallel or symmetric about the longitudinal axis 134, although in some examples, some features can be.

As shown in FIG. 1A, in some examples, the augment 100 can be formed of a first extension extending away from the first end portion 130 in a first direction (e.g., to mounting element 140c), a second extension extending away from the first end portion 130 in a second direction (e.g., to mounting element 140f), and a third extension can be disposed between the first extension and the second extension (e.g., shown along longitudinal axis 134). A crossmember 141 can extend from the first extension to the second extension. Any of the first, second or third extensions can have a contourable portion (e.g., 150a-h). In between the extensions can be cutouts 131 without any material.

As shown in FIGS. 1A and 1B, the first end portion 130 of the augment 100 can have a first portion 136 of a locking mechanism that can be adapted to be fixed to an acetabular shell 90, hereinafter shell 90, such as the shell 90 shown in FIGS. 2A and 2B. The shell 90 can be generally semi-spherical in shape and have a first shell surface 93 opposite a second shell surface 95.

Figure 2A:
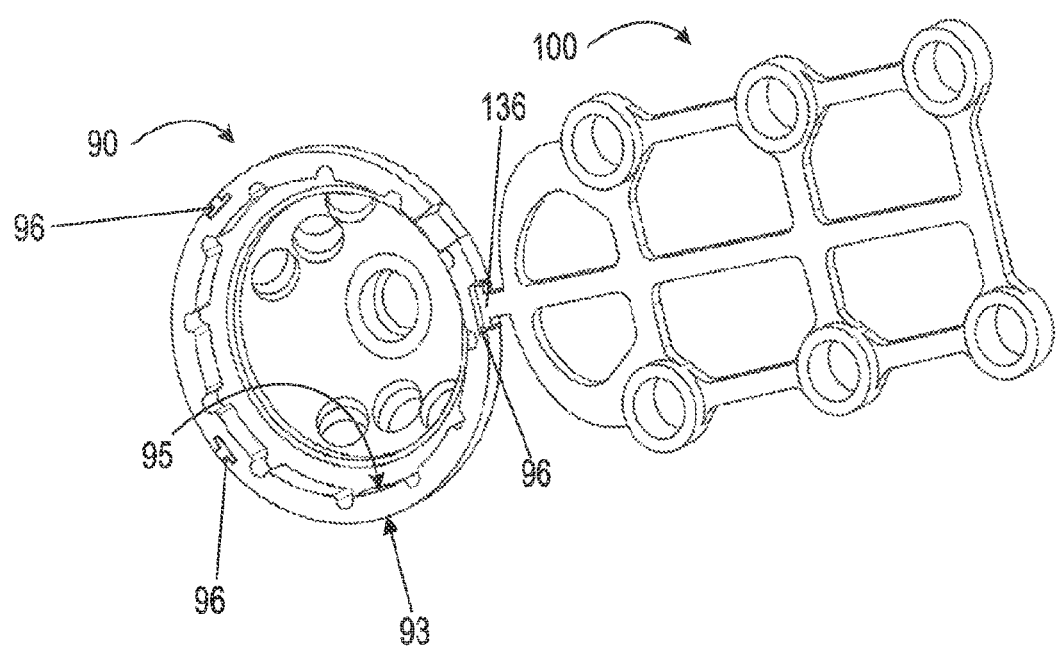
FIG. 2A is a top perspective view of the illustrative augment of FIG. 1A coupled to an illustrative shell, in accordance with at least one example.
Figure 2B:
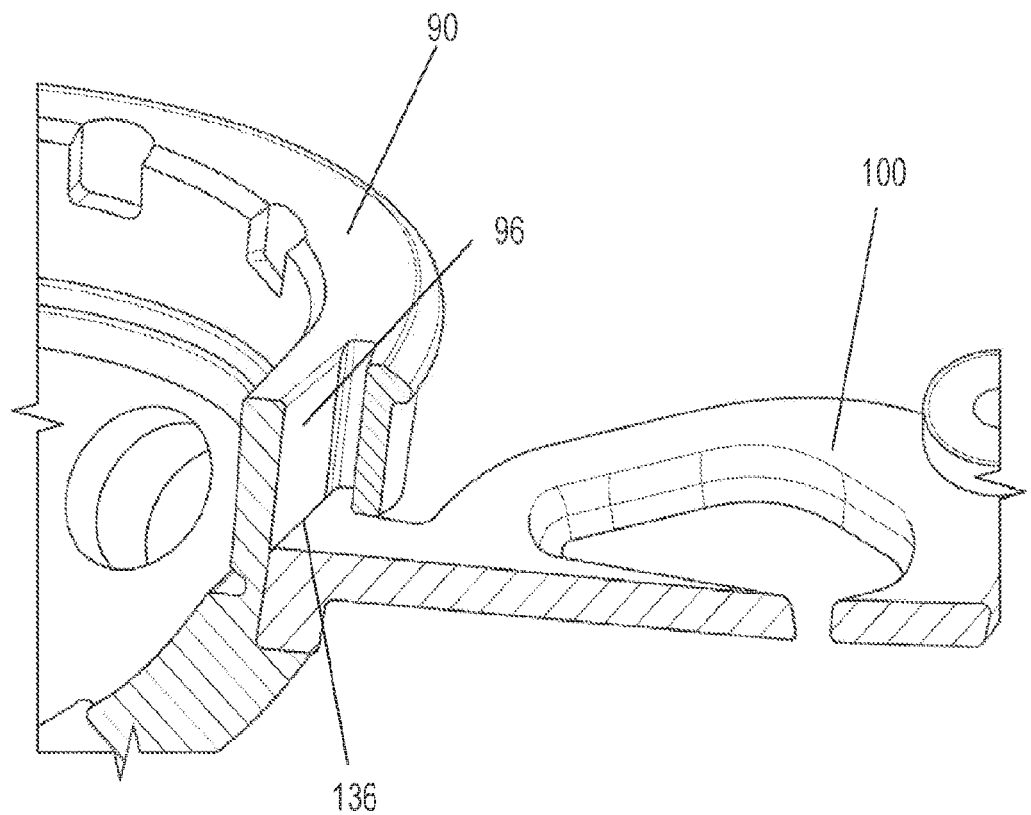
FIG. 2B is a close up perspective cross-sectional view at section A along line B-B' of FIG. 2.

The locking mechanism (e.g., combination of 96, 136) shown generally in FIGS. 2A and 2B, can be included to secure the augment 100 to the shell 90. Illustrative examples of a locking mechanism for securing an augment to a shell will be described further with reference to FIGS. 4-6. In the illustrative examples of FIGS. 4-6 the locking mechanism is provided as a first portion and a second portion that can be moved from an unlocked state to a locked state. The first portion of the locking mechanism (e.g., 136) can be a male portion located on the augment, and a second portion of the locking mechanism (e.g., 96) can be a female portion provided as a recess (e.g., receptacle, guide, restrictor, slot or groove, etc.) that can be located on the first shell surface 93 of shell 90. The first portion 136 of the body 120 (e.g., 1A) of the augment 100 can be aligned with the second portion 96, and the first portion 136 can be inserted by sliding into the second portion 96.

In addition to a locking mechanism to couple the augment 100 to the shell 90, to fasten the augment 100 to bone 1 (e.g., FIG. 3), the augment 100 can include any number of mounting elements (e.g., 140a-f) as shown in FIG. 1A. Each of the mounting elements 140a-f can have an opening extending through the body from the first surface 122 to the second surface 124. In some examples, the mounting elements 140a-f can be described as being arranged along the longitudinal axis 134. In some examples, the mounting elements 140a-f can be arranged serially (e.g., in series, spaced apart, one after the other) along the longitudinal axis 134. While the mounting elements 140a-f can be described as extending along the longitudinal axis 134, this does not mean that all of the various mounting holes 140a-f described herein are necessarily symmetric about, aligned to, or aligned parallel to the longitudinal axis 134, or even aligned with one another. The longitudinal axis 134 merely provides a general directional relationship of the holes with respect to each other and location along the augment 100 and in relation to the shell it supports. However, in some examples, any of the mounting elements or other features can be aligned to or symmetric about the longitudinal axis 134, or arranged generally along the longitudinal axis 134 on opposing sides of the axis as shown in FIG. 1A. In some examples, the mounting elements 140a-f can be provided without an opening extending through the body 120 of the augment 100 depending on the type of fastener or material used to fasten the augment 100 to the bone 1.

To facilitate improved customization of the augment 100 to a patient, one or more contourable portions 150a-h can be provided. In shown in FIG. 1A, the contourable portions 150a-h can interconnect and support the mounting elements 140a-f.

In some examples, and as shown in FIG. 1A, any of the contourable portions 150a-h of the augment 100 can be identified with a contourable portion marker 151 (e.g., markers at 150b) indicating a location of a bendable portion of the augment. The contourable portions 150a-h can be located, for example, in between the first mounting element 140a and the second mounting element 140b. The one or more contourable portions 150a-h can be locations on the body 120 of the augment 100 where a portion (e.g. predetermined portion) of the augment 100 can be contoured (e.g., bent) in order to contour the shape of an augment 100 to better match the bone 1 (FIG. 3) surface that the augment 100 will be mounted to for a particular patient. Reasons the surgeon would contour the shape of the augment 100 can include: the augment 100 shape is too planar or too curved compared to the patient's bone 1, or the patient has a lack of good bone 1 to fasten to in that portion of the augment 100, and by bending the augment 100, the augment can more closely approximate the shape and location of the available bone 1.

Figure 3:
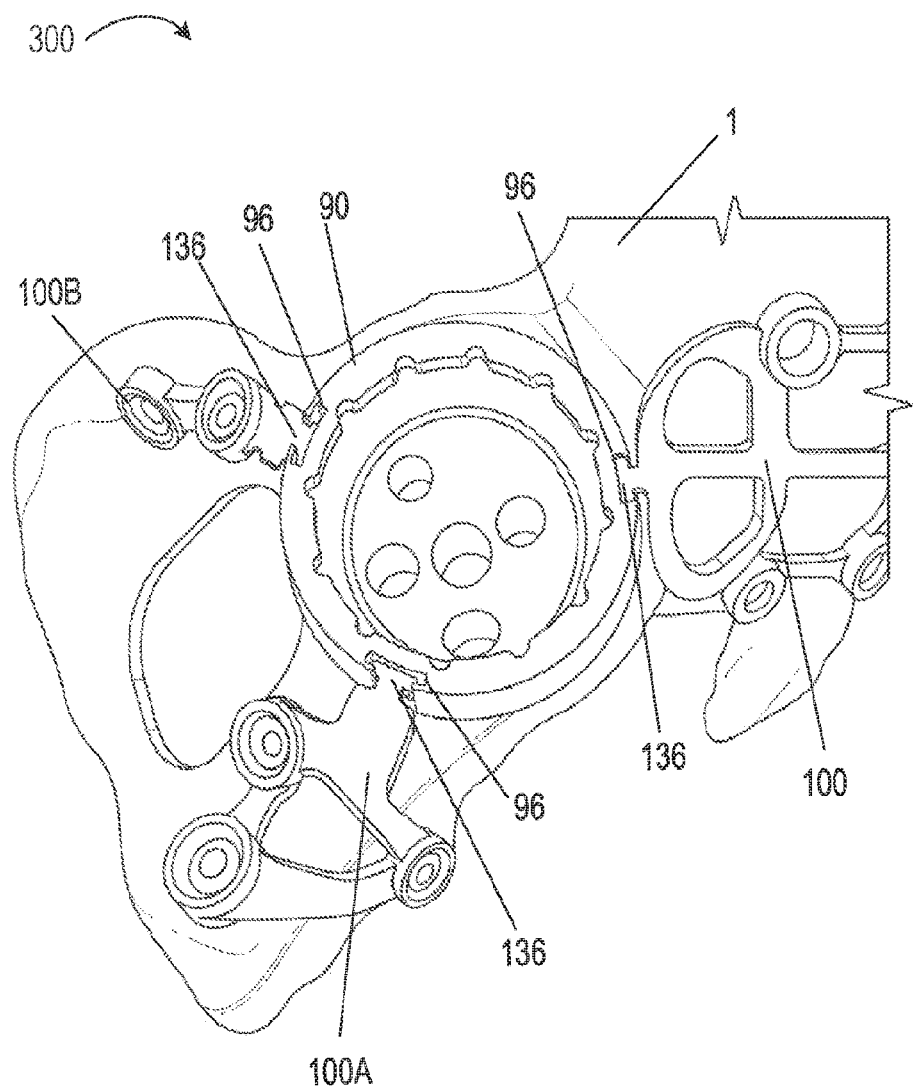
FIG. 3 is a top perspective view of illustrative augments, including the illustrative augment of FIG. 1A, arranged around an acetabular shell and conformed to a hip bone, in accordance with at least one example.

FIG. 3 shows top perspective view of illustrative augments, including the illustrative augment 100 of FIG. 1A, arranged around an acetabular shell 90. The augments 100, 100B, 100C are coupled to the shell 90 at respective locking mechanisms (e.g., 96, 136) and are conformed to a hip bone, in accordance with at least one example. Here, the augments 100, 100B and 100C have been bent to match the shape of the bone 1 of the particular patient. This provides the surgeon the ability to optimize the fit and strength of the attachment of the augment to the host bone with an "off the shelf" augment. In addition to the fit being optimized, the need to remove additional host bone in order to achieve a natural implant positioning and orientation can be reduced. Achieving proper positioning of the shell 90 can lead to improved hip kinematics in the patient.

Returning to FIG. 1A, in some examples, any of the contourable portions 150a-h can be identified (e.g., labeled, engraved, etched, printed etc.) with a contourable portion marker 151 that can indicate a location on the body 120 that can be more contourable (e.g., bendable) than other portions of the body 120. The contourable portions 150a-h can be more bendable than the mounting elements 140a-f, such as bendable by a lower amount of force. The contourable portions 150a-h can also be portions of the augment 100 that can be bent to conform to the bone 1 of the user without degrading performance of the augment 100. In some examples, performance can be described as the ability to support a shell (e.g., 90, FIG. 2), or the strength of the attachment to the bone and/or the shell, or the resistance to movement of the shell. In particular, the contourable portion (e.g., 150a) can be a location that can be more contourable than the portions adjacent to (e.g., the portions next to, or directly adjacent to) the contourable portion 150a. For example, the contourable portion marker 151 can be located in between the first end portion 130 of the augment and a first mounting element 140a (FIG. 1A). In other examples, and as shown in FIG. 1A the contourable portion (e.g., 150b) can be sandwiched between the first mounting element 140a and the second mounting element 140b. The contourable portions150a-h can include characteristics that make the body 120 more easily bendable at the contourable portions 150a-h than, for example, the portion of the first mounting element 140a and the second mounting element 140b that are directly adjacent to the contourable portion 150b.

As perhaps most clearly shown in FIG. 1B, the augment 100 can have a thickness defined from the first surface 122 to the second surface 124. The thickness can be relatively constant, or, as shown in FIG. 1B, the thickness can vary.

To facilitate bending, the one or more contourable portions 150a-h can be a region of the body 120 having a decreased thickness of the body 120. The thickness in the area of the contourable portion 150a-h can be thinner than the first and second mounting elements 140a, 140b, or, it can be thinner than the majority of the body 120. Other examples of mechanisms that facilitate bending at the contourable portion 150a-h can include: different material characteristics, porosity, compositions or geometry at the contourable portion 150a-h compared to other portions of the body 120. Geometric features can also include perforations through the thickness of the body 120 at the contourable portion 150a-h, or specific bending features that are not loaded under normal use, but that can be intentionally activated to initiate bending by the surgeon.

While the contourable portions 150a-h are shown as extending in a generally straight line, such as directly from one mounting element to another mounting element, or as being parallel or perpendicular to longitudinal axis 134, the contourable portions 150a-h can be located in any suitable location on the augment and can extend in any suitable direction, be straight or curved, of consistent thickness or variable thickness, depending on the application.

The features of the augments described herein can be incorporated into different types of augments and in different forms. As shown in the example of FIGS. 1A and 1B, the augment 100 can be a flange-type augment. For example, in the augment of FIGS. 1A and 1B, the body 120 can be adapted to structurally support an acetabular shell (e.g., 90, FIGS. 2A and 2B) that can be implanted in a patient having pelvic discontinuities. Example augments can support a Paprosky type II defect. Example augments can include structural augments to address superior segmental and cavitary defects, among others. The example augment can beneficially accomplish this in more patients, without fully custom patient-matched implants or augments.

In some examples, and as previously described, the augment 100 can include a porous material that promotes boney ingrowth (e.g., supports boney ingrowth). In some examples, the augment 100 can be made partly or entirely of the porous material, partly or entirely of a solid material that is generally non-porous (e.g., solid metal, solid polymeric material), or a combination of both solid and porous materials.

In the example of FIGS. 1A and 1B, as identified in FIG. 1B, the first surface 122 can include a smooth, generally non-porous surface (e.g., most or all of the first surface can be a smooth, non-porous surface) and can be adapted to face away from the bone surface when implanted. One benefit of the first surface 122 being smooth can be that it allows the first surface 122 not to irritate the tissues, including muscle tissue that is adjacent the augment 100 and covering the bone.

In contrast to the smooth, generally non-porous first surface 122, the second surface 124 can be adapted to mate with the bone surface when implanted and can include the porous material that promotes boney ingrowth. One benefit of having the second surface 124 being porous material can be that it promotes boney ingrowth for better fixation to the bone. Boney ingrowth into the porous material can provide a stronger structural connection to the bone as the bone grows into the porous material over time.

Another benefit of the porous material at the second surface 124 can be that the porous surface exhibits a high coefficient of friction against the bone which can provide enhanced stability. In the example of FIGS. 1A and 1B, as identified in FIG. 1B, the first surface 122 can have a first coefficient of friction, and the second surface 124 can have a second coefficient of friction. The first coefficient of friction can be less than the second coefficient of friction. This arrangement can improve the grip between the bone and the second surface 124 of the augment 100, while allowing the muscle tissue over the hip bone to glide over the first surface 122 of the augment 100.

To facilitate boney ingrowth, any of the augments described herein can be formed of a three-dimensional structure that promotes (e.g., supports) boney ingrowth. For example, a highly porous, three-dimensional metallic structure can be provided that incorporates one or more of a variety of biocompatible metals such as but not limited to titanium, a titanium alloy, cobalt chromium, cobalt chromium molybdenum, tantalum, a tantalum alloy, niobium, or alloys of tantalum and niobium with one another or with other metals. Such structures are particularly suited for contacting bone and/or soft tissue, and in this regard, can be useful as bone substitutes and other implants and implant components that are receptive to cell and tissue ingrowth, for example, by allowing boney tissue or other tissue to grow into the porous structure over time to enhance fixation (e.g., osseointegration) between the structure and surrounding bodily structures. According to certain examples of the present disclosure, an open porous metal structure, or a portion thereof, can have a bulk porosity as low as 55%, 65%, or 75% or as high as 80%, 85%, or 90%, or within any range defined between any pair of the foregoing values, and in this regard, such structures can provide lightweight, yet strong porous implants. Certain porous metal structures, despite having such high porosities, are capable of withstanding extreme mechanical loads at the time of implantation and over long periods of time, for example, where a highly porous, three-dimensional metallic structure is forcefully impacted and press fit into a bone, by itself or connected to another implant, and maintains its shape during impaction and following many months or years of service in the body. Such structures can be manufactured according to any suitable technique or process. An example of an open porous metal structure is produced using Trabecular Metal™ Technology available from Zimmer, Inc., of Warsaw, Ind. Trabecular Metal™ is a trademark of Zimmer, Inc. Such a material can be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861 and in Levine, B. R., et al., "Experimental and Clinical Performance of Porous Tantalum in Orthopedic Surgery", Biomaterials 27 (2006) 4671-4681, the disclosures of which are expressly incorporated herein by reference.

In some instances, a highly porous, three-dimensional metallic structure will be fabricated using a selective laser sintering (SLS) or other additive manufacturing-type process such as direct metal laser sintering or electron beam melting. In one example, a three-dimensional porous article is produced in layer-wise fashion from a laser-fusible powder, e.g., a single-component metal powder, which is deposited one layer at a time. The powder is fused, remelted or sintered, by the application of laser energy that is directed to portions of the powder layer corresponding to a cross section of the article. After the fusing of the powder in each layer, an additional layer of powder is deposited, and a further fusing step is carried out, with fused portions or lateral layers fusing so as to fuse portions of previous laid layers until a three-dimensional article is complete. In certain examples, a laser selectively fuses powdered material by scanning cross-sections generated from a 3-D digital description of the article, e.g., from a CAD file or scan data, on the surface of a powder bed. Complex geometries can be created using such techniques, and in some instances, net shape and near net shape implants are constructed. In some examples, a non-porous or essentially non-porous base substrate will provide a foundation upon which a three-dimensional porous structure will be built and fused thereto using a selective laser sintering (SLS) or other additive manufacturing-type process. Such substrates can incorporate one or more of a variety of biocompatible metals such as any of those disclosed herein.

Generally, a highly porous, three-dimensional metallic structure will include a large plurality of ligaments that define open voids (e.g., pores) or channels between the ligaments. The open spaces between the ligaments form a matrix of continuous channels having few or no dead ends, such that growth of soft tissue and/or bone through the open porous metal is substantially uninhibited. According to some aspects of the present disclosure, exterior surfaces of an open porous metal structure can feature terminating ends of the above-described ligaments. Such terminating ends can be referred to as struts, and they can generate a high coefficient of friction along an exposed porous metal surface. Such features can impart an enhanced affixation ability to an exposed porous metal surface for adhering to bone and soft tissue. Also, when such highly porous metal structures are coupled to an underlying substrate, a small percentage of the substrate can be in direct contact with the ligaments of the highly porous structure, for example, approximately 15%, 20%, or 25%, of the surface area of the substrate can be in direct contact with the ligaments of the highly porous structure.

A highly porous, three-dimensional metallic structure can be fabricated such that it comprises a variety of densities in order to selectively tailor the structure for particular orthopedic applications, for example, by matching the structure to surrounding natural tissue in order to provide an improved matrix for tissue ingrowth and mineralization. Such structures can be isotropic or anisotropic. In this regard, according to certain examples, an open porous metal structure can be fabricated to have a substantially uniform porosity, density, void (pore) size, pore shape, and/or pore orientation throughout, or to have one or more features such as porosity, density, void (pore) size, pore shape, and/or pore orientation being varied within the structure, or within a portion thereof. For example, an open porous metal structure can have a different pore size, pore shape, and/or porosity at different regions, layers, and surfaces of the structure. The ability to selectively tailor the structural properties of the open porous metal enables, for example, tailoring of the structure for distributing stress loads throughout the surrounding tissue and promoting specific tissue ingrown within the open porous metal. In some instances, a highly porous, three-dimensional metallic structure, once formed, will be infiltrated and coated with one or more coating materials such as biocompatible metals such as any of those disclosed herein.

In some examples, the porous metal structure can be a formed from a titanium alloy using an additive manufacturing process, such as with OsseoTi™, which is commercially available from Biomet Manufacturing, LLC (Warsaw, Ind., USA). Briefly, however, OsseoTi™ is highly biocompatible, has high corrosion resistance and includes a highly interconnected porous architecture that mimics the porous structure of human cancellous bone, which can enhance bone integration and in-growth. In one exemplary implementation, OsseoTi™ can include a porous construct with a porosity.

FIG. 3 is a top perspective view of an illustrative system 300 of augments 100, 100B, 100C arranged around an acetabular shell 90 at a hip bone 1 after the augments have been bent and contoured to the patient's bone, in accordance with at least one example. The augments 100, 100B and 100C can be fixedly coupled to the shell 90 by the locking mechanism described with respect to augment 100, and as will be further described with respect to FIGS. 3-6.

As shown in FIG. 3, the acetabular shell 90 can be arranged at an acetabulum of the hip bone and one or more of the augments 100, 100A, 100B can be arranged around the shell 90 to support the shell 90. The example of FIG. 3 depicts a system 300 having three augments including a first augment 100, a second augment 100A, and a third augment 100B. Three augments are shown in the system 300, but any suitable number of augments can be used. In some examples, a single augment can be used, or any of the augments can be used in combination with other augments different than the augments shown and described herein.

Any of the features shown and described with reference to the augment 100 of FIGS. 1A-1B, can be incorporated into any of the first, second and third augments 100B and 100C (e.g., the augments) of FIG. 3, or any other augments described herein. Like the augment 100 of FIGS. 1A-1B, and with reference to element numbers of FIGS. 1A-1B, each of the augments 100, 100B and 100C can include a body (e.g., 120) having a first surface (e.g., 122) adapted to face away from the bone 1 and a second surface (e.g., 124) opposite the first surface (e.g., 122) adapted to face the bone 1. Other augments described with reference to FIGS. 4-6 can also have these and other characteristics of the augment 100.

Various locking mechanisms will be described with reference to FIGS. 4-6. The illustrative locking mechanisms can have a first portion that is generally located on the augment and may be integrally formed into, fixedly coupled to, or in a fixed relationship with the body of the augment, and a second portion that is generally located on the shell. However, in some examples, the features described with respect to the first portion can be incorporated into the shell and the features of the second portion can be incorporated into the augment.

Figure 4:
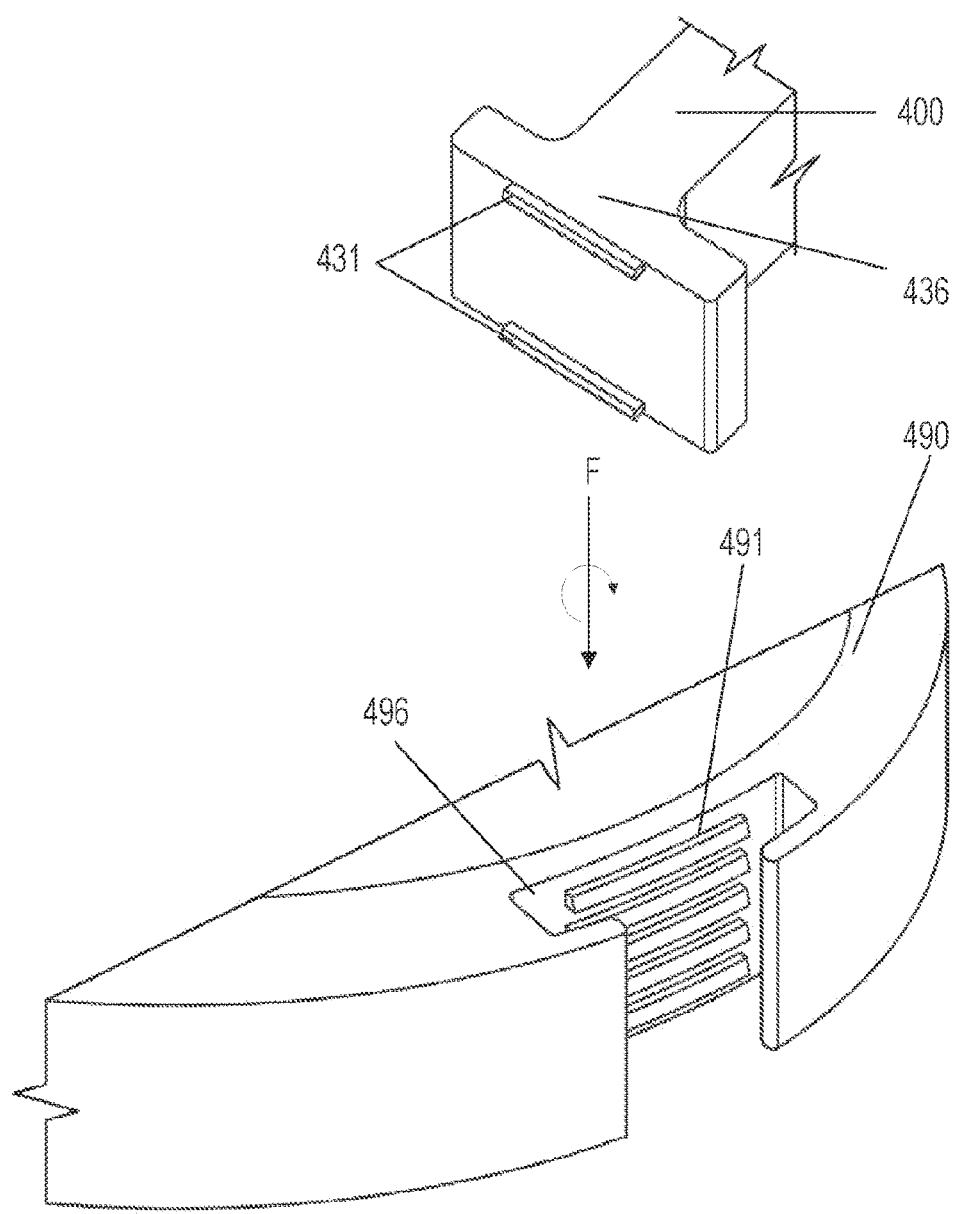
FIG. 4 is a close up perspective view of an illustrative locking mechanism in an unengaged, unlocked arrangement, in accordance with at least one example.

As shown in FIG. 4, an illustrative locking mechanism having a first portion 436 shown on a partial view of augment 400 (e.g., can be similar to augment 100) and a second portion 496 shown on partial view of shell 490 (e.g., can be similar to shell 90) can include a ratchet-style locking mechanism. In some examples, the first portion 436 can include one or more pawls 431.

In order to move the locking mechanism 436, 496 into a locked state (e.g., fixed in the arrangement shown in FIG. 2A), the second portion 496 can include teeth 491 configured such that the one or more pawls 431 can be slid along and engaged with the teeth 491. For example, the first portion 436 can be aligned with and inserted into the second portion 496 (e.g., 96, FIG. 1B) and slid downward relative to the second portion 496 by a force F such that the pawls 431 pass across the teeth 491, engaging one another to create the locked state. The locked state is created by the one or more pawls 431 passing across the teeth 491 easily in one direction, but one or more pawls 431 and the teeth 491 having geometry that restricts movement in the opposite direction, thereby creating the locked state. In some examples, the one or more pawls 431 can be part of the second portion 496 of the locking mechanism and the teeth 491 can be part of the first portion 436 of the locking mechanism. In the locked state, the first portion 436 can be described as being operably engaged with the second portion 496.

With continued reference to FIG. 4, and with support from the example augment 100 shown in FIG. 1A, the relationship of the first portion 436 as part of an overall augment, such as the augment 100 of FIG. 1A, will be described. In some examples, including other examples described herein, in the locked state, the first portion 436 of the locking mechanism can be integrally formed into the first end portion 130 of the body 120 of the augment 100. This integrally formed first portion 130 of the body 120 can be the portion of the augment 100 (shown in partial view as 400 in FIG. 4) that is received by the shell 490.

In other words, the first portion 436 of the first end portion 130 can be fixedly coupled or otherwise fixedly incorporated into the body 120 of the augment 100 such that no relative translation (e.g., movement) is required between the first portion 436 of the first end portion 130, and the body 120 of the augment 100, to move from the unlocked state (e.g., FIG. 4) to the locked state (e.g., fixed in the arrangement of FIG. 2A). Such an arrangement can facilitate an improved coupling of the augment 400 to the shell 490.

Figure 5:
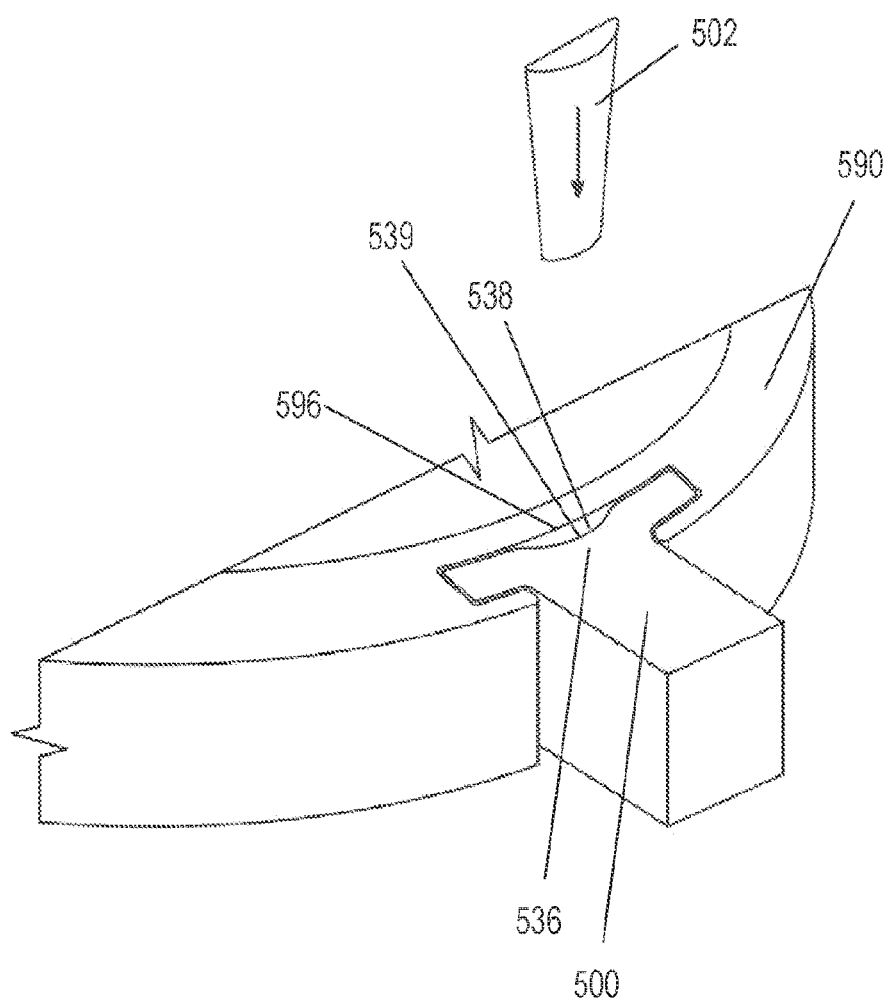
FIG. 5 is a close up perspective view of another illustrative locking mechanism in an unengaged, unlocked arrangement, in accordance with at least one example.

As shown in FIG. 5, an illustrative locking mechanism can include a wedge-style locking mechanism. In some examples, a wedge 502 can be inserted between a first locking portion 536 of an augment 500 (e.g., can be similar to 100) and a second portion 596 of a shell 590 (e.g., can be similar to 90). In the example of FIG. 5, the first end portion 530 can be shaped to be received in the second end portion 596, such as a recess or receptacle (e.g., FIGS. 2A and 2B, 96) of the shell 590 (e.g., FIGS. 2A and 2B, 90). Although the first portion 536 of the locking mechanism can be generally complimentary to the shape of the recess of the second portion 596 in the shell 590, in some examples, the first end surface 538 can include a wedge recess 539 to accept insertion of the wedge 502. The wedge recess 539 can allow for insertion of a wedge 502. The first end surface 138 represents merely one example shape, location and arrangement that can be used for a wedge-style locking mechanism. Any suitable shape, location or arrangement for the first end surface 538, including locating the wedge recess 539 on a different surface of the first end portion 130, such that the wedge recess 539 can engage with the wedge 502 to create a locked state of the locking mechanism can be used.

Insertion of the wedge 502 by force (e.g., arrow) causes the first portion 536 to move radially outward with respect to the second portion 596 of the shell, increasing the force of the first portion 536 compressing against the second portion 596, thereby wedging and compressing the first portion 536 against the second portion 596 to create the locked state.

Figure 6:
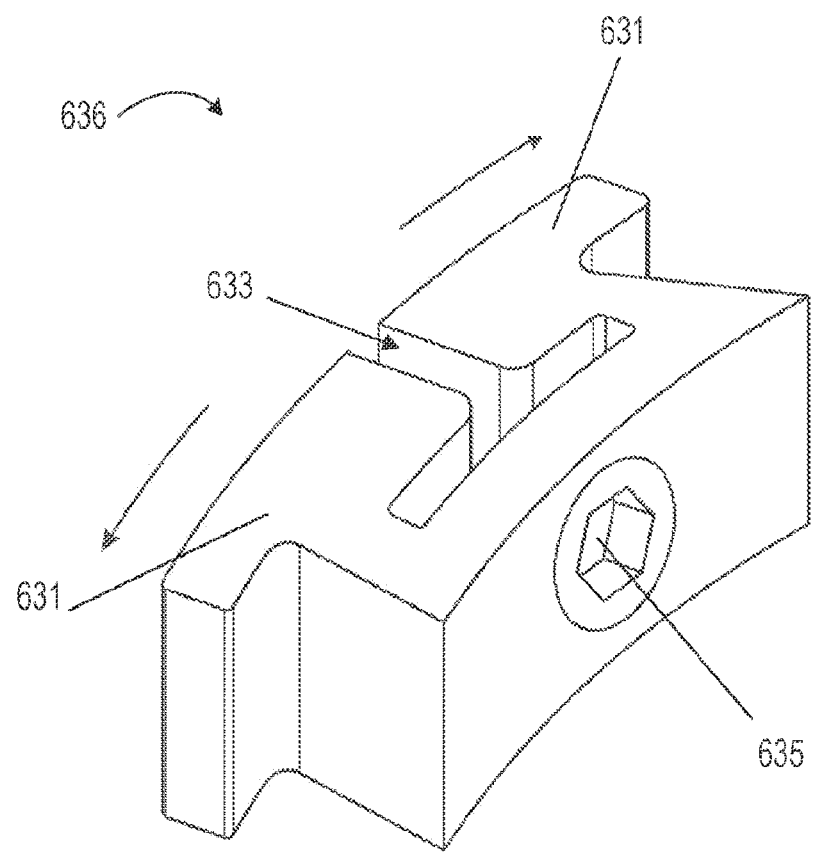
FIG. 6 is a close up perspective view of a first (e.g., male) portion of another illustrative locking mechanism, in accordance with at least one example.

As shown in FIG. 6, an illustrative first portion 636 of a locking mechanism that can be part of an augment (e.g., such as the augment 100, 400 or 500) can include two expandable fingers 631. The expandable fingers 631 can be separated by a gap 633. To expand the fingers 631, a screw 635, such as a tapered screw, can extend through the first portion 636 and into the gap 633. The screw 635 can be turned in order to drive the expandable fingers 631 further apart, thereby pressing the expandable fingers 631 against the second portion (e.g., 96, FIGS. 2A and 2B). In the example of FIG. 6, the augment shape can include clearance holes, bends, or other suitable features to allow access to the screw 635. Other fasteners besides screws can be used, such as a push rivet (e.g., christmas tree fastener).

Figure 7:
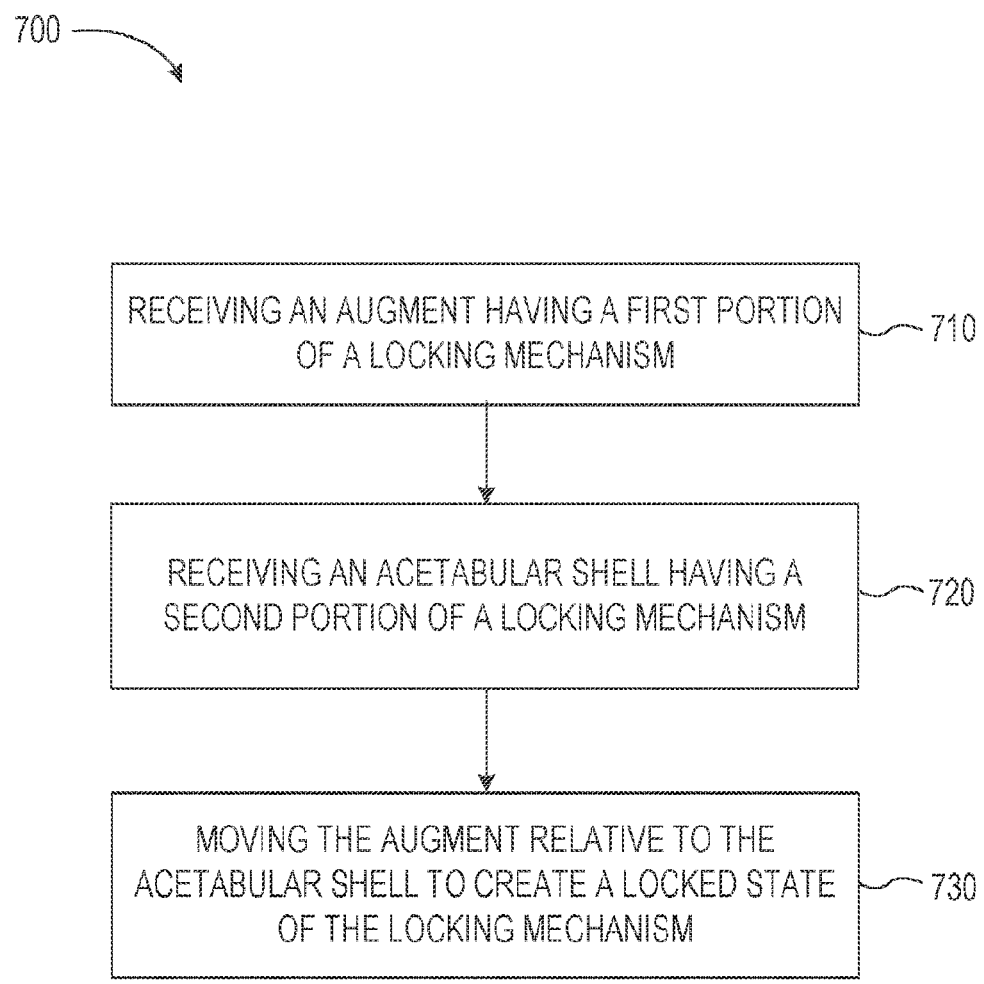
FIG. 7 is a flow chart illustrating a method of securing an augment to an acetabular shell.

FIG. 7 is a flow chart illustrating a method of securing an augment to an acetabular shell, of FIGS. 1A and 1B, the augments and shell of FIGS. 2A and 2B and the locking mechanisms of FIGS. 3-6, in accordance with at least one example.

Step 710 can include receiving an augment having a first portion of a locking mechanism as described herein.

Step 720 can include receiving an acetabular shell having a second portion of a locking mechanism as described herein.

Step 730 can include moving the augment relative to the acetabular shell to align the first portion with the second portion, and the sliding the first portion relative to the second portion to create a locked state of the locking mechanism. For example, inserting the first portion into the second portion, such as by the example locking mechanisms of FIGS. 4-6, or any other suitable locking mechanism.

FIG. 8 is a flow chart illustrating a method of using augments to secure an acetabular shell to a bone of a patient for a total hip arthroplasty, such as the augments of FIGS. 1A-1B, the augments and shell of FIGS. 2A and 2B, and the locking mechanisms of FIGS. 3-6, in accordance with at least one example.

Step 810 can include assessing a bone of a patient for an acetabular bone defect and identifying the type of acetabular bone defect. Based on the type of acetabular bone defect identified in the patient, step 820 can include selecting a type of an augment, such as the augments and augment features described above with respect to FIGS. 1A, 1B, 2A, 2B and 3-6, to address the type of acetabular bone defect that was identified in the patient.

Step 830 can include preparing the bone for the augment. This can include reaming the acetabulum to prepare it to receive a shell or cup of the hip prosthesis.

Step 840A can include determining if a portion of the augment is to be contoured. The portion of the augment to be contoured can be a predetermined portion or any other contourable portion. For example, the portion can be predetermined in the sense that, one or more contourable portions are predetermined and are marked with markers identifying where the predetermined contourable portions or suggested bend locations are positioned, as previously described with reference to the examples of FIGS. 1A, 1B, 2A and 2B. Once the predetermined portion or another contourable portion to be contoured is determined, step 840B can include contouring the contourable portion of the augment.

As previously described with respect to the example augments of FIGS. 1A, 1B 2A and 2B, in some examples of step 840B, the contouring step can include contouring (e.g., bending or otherwise modifying) a contourable portion of the augment that extends between, for example, a first end portion and a bone attachment (e.g., a first bone attachment or first mounting element). The contourable portion can also extend between, the bone attachment and a second bone attachment. In some examples of step 840B, the contouring step can include contouring a contourable portion of the augment that extends between the second bone attachment and a third bone attachment or a second end portion of the augment.

Various methods and processes can be used to contour the predetermined portion. In some examples, where the augment can be formed partly or completely of a porous material that promotes boney ingrowth, the contouring step can be complicated by this material. The voids in the porous material, the complicated 3-dimensional shapes, and the hardness, brittleness, fragility or other material characteristics of the augments can require methods of contouring that are tailored to the particular augment to be modified.

Processes for contouring the contourable portion and smoothing of edges can include the use of: plate benders, heating steps, cooling steps, curved molds, vices, hammers, or any other suitable tool or process appropriate for the material, shape and porosity of the augment. In some examples, methods and tools that can apply a consistent force to gradually bend the contourable portion by applying a consistent force can be used. In some examples, such as the example augment 100 of FIG. 3, step 840B can include contouring more than one contourable portion of the augment. For example, in the example of the augment 100 of FIG. 3, the augment 100 has multiple contourable portions. In such an example a contourable portion can be contoured at the first extension but not the second extension, contoured at the second extension but not the first extension, or contoured at both the first and second extensions.

Step 850 can include orienting the remaining body of the augment at the bone. Examples of locations where the augment can be oriented on the bone can include: a superior position on an ilium of the bone, or an inferior position on an ischium or ramus of the bone. Any other suitable location for an augment can also be used.

Step 860 can include securing the augment to the bone at one of the bone attachments, such as by screws inserted through holes in the augment. In order for the augment to provide support for the shell, step 870 can include securing the augment to an acetabular shell by any of the features and methods described with respect to FIGS. 4-6 as well as FIGS. 1A, 1B, 2A, 2B and 3. For example, the augment can be secured to the shell by any of the locking mechanisms described in FIGS. 4-6, or other suitable locking mechanisms. Alternatively the augment can be secured to the shell by cement or screw attachment. Step 880 can include securing the acetabular shell to the bone, for example, by cement and/or a fastener such as a screw. If using a liner, step 890 can include securing a liner to the acetabular shell, such as by cemented attachment or snap fit.

The above detailed description includes references to the accompanying drawings, which form a part of the detailed description. Such examples can include elements in addition to those shown or described. However, examples in which only those elements shown or described are provided are also contemplated. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) be used in combination with each other. Other examples can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

VARIOUS NOTES AND EXAMPLES

To better illustrate the devices and methods disclosed herein, a non-limiting list of embodiments is provided herein.

Example 1 is an acetabular shell and augment system for attachment to a bone, the system comprising: an augment extending from a first end portion to a second end portion and having a first surface and a second surface opposite the first surface, the first end portion including a first portion of a locking mechanism; and a shell having first thickness defined between a first shell surface and a second shell surface, the shell including a second portion of the locking mechanism, wherein the second portion of the locking mechanism is a recess that extends into the first shell surface, and wherein the first portion of the locking mechanism and the second portion of the locking mechanism are adapted to move relative to one another from an unlocked state to a locked state to fixedly couple the augment to the shell.

In Example 2, the subject matter of Example 1 optionally includes wherein the recess formed in the shell is sized and shaped to receive the first end portion of the augment.

In Example 3, the subject matter of any one or more of Examples 1-2 optionally include wherein the first end portion comprises a portion of a ratchet-style locking mechanism having a pawl adapted to engage teeth in the recess of the acetabular shell.

In Example 4, the subject matter of any one or more of Examples 1-3 optionally include wherein the first end portion comprises a portion of a wedge-style locking mechanism having a wedge recess in a first end surface, wherein the wedge recess is adapted to allow insertion of a wedge between the first end surface and the first shell surface to drive the wedge-style locking mechanism into the locked state.

In Example 5, the subject matter of any one or more of Examples 1-4 optionally include wherein the first end portion comprises an expansion screw style locking mechanism having expandable fingers including a flange, the expandable fingers adapted to be driveable into the locked state.

In Example 6, the subject matter of any one or more of Examples 1-5 optionally include the augment further comprising: a first mounting element and a second mounting element, each of the first and second mounting elements having an opening extending through the augment from the first surface to the second surface, wherein each of the first and second mounting elements are adapted to be fixed to the bone; and a contourable portion located between the first and second mounting elements, wherein the contourable portion has a contourable portion thickness defined between the first surface and the second surface, wherein the mounting element has a mounting element thickness defined between the first surface and the second surface, and wherein the contourable portion thickness is less than the mounting element thickness.

Example 7 is a method for securing an augment to an acetabular shell, the method comprising: receiving an augment having first surface and a second surface opposite the first surface, the augment extending from a first end portion to a second end portion, the first end portion including a first portion of a locking mechanism; receiving an acetabular shell having a second portion of the locking mechanism; and moving the first portion of the locking mechanism relative to the second portion of the locking mechanism to engage and fixedly couple the first portion of the locking mechanism and the second portion of the locking mechanism into a locked state.

In Example 8, the subject matter of Example 7 optionally includes wherein moving the first portion of the locking mechanism relative to the second portion of the locking mechanism includes inserting the first portion into a receptacle of the second portion.

In Example 9, the subject matter of any one or more of Examples 7-8 optionally include wherein moving the first portion of the locking mechanism relative to the second portion of the locking mechanism comprises moving a pawl of the locking mechanism relative to teeth of the locking mechanism.

In Example 10, the subject matter of any one or more of Examples 7-9 optionally include wherein moving the first portion of the locking mechanism relative to the second portion of the locking mechanism includes inserting a wedge between the first and second portions of the locking mechanism.

In Example 11, the subject matter of any one or more of Examples 7-10 optionally include wherein moving the first portion of the locking mechanism relative to the second portion of the locking mechanism includes driving expandable fingers of the first portion into the locked state.

In Example 12, the subject matter of any one or more of Examples 7-11 optionally include wherein moving the first portion of the locking mechanism relative to the second portion of the locking mechanism includes screwing a tapered screw to drive expandable fingers of the first portion of the locking mechanism into the locked state.

In Example 13, the subject matter of any one or more of Examples 7-12 optionally include assessing a patient for an acetabular bone defect and identifying a type of acetabular bone defect; selecting a type of an augment based on the type of the acetabular bone defect identified in the patient, the augment comprising a contourable portion and a mounting element, the contourable portion and the mounting element extending from the first surface to the second surface; and bending the contourable portion, wherein the contourable portion has a contourable portion thickness defined between the first surface and the second surface, wherein the mounting element has a mounting element thickness defined between the first surface and the second surface, and wherein the contourable portion thickness is less than the mounting element thickness.

Example 14 is an augment for supporting an acetabular shell at a bone, the augment comprising: a body having a first surface and a second surface opposite the first surface, the body extending from a first end portion to a second end portion, wherein the first end portion is adapted to be fixed to the acetabular shell; a mounting element having an opening extending through the body from the first surface to the second surface, wherein the mounting element is adapted to be fixed to the bone; and a contourable portion located between the first end portion and the mounting element.

In Example 15, the subject matter of Example 14 optionally includes wherein the contourable portion is more bendable than the mounting element.

In Example 16, the subject matter of any one or more of Examples 14-15 optionally include a second mounting element having a second opening extending through the body from the first surface to the second surface, wherein the contourable portion is located between the mounting element and the second mounting element.

In Example 17, the subject matter of any one or more of Examples 14-16 optionally include wherein the first end portion comprises a portion of a locking mechanism.

In Example 18, the subject matter of any one or more of Examples 14-17 optionally include wherein the first end portion comprises a portion of a friction-style locking mechanism.

In Example 19, the subject matter of any one or more of Examples 14-18 optionally include wherein the first end portion comprises a portion of a ratchet-style locking mechanism having a pawl adapted to engage teeth in a receptacle of the acetabular shell.

In Example 20, the subject matter of any one or more of Examples 14-19 optionally include wherein the first end portion comprises a portion of a wedge-style locking mechanism having a wedge recess in a first end surface, wherein the wedge recess is adapted to allow insertion of a wedge between the first end surface and a first shell surface of the acetabular shell to drive the wedge-style locking mechanism into a locked state.

In Example 21, the subject matter of any one or more of Examples 14-20 optionally include wherein the first end portion comprises an expansion style locking mechanism having expandable fingers including a flange, the expandable fingers adapted to be driveable into a locked state.

In Example 22, the subject matter of any one or more of Examples 14-21 optionally include wherein the contourable portion has a contourable portion thickness defined between the first surface and the second surface, wherein the mounting element has a mounting element thickness defined between the first surface and the second surface, and wherein the contourable portion thickness is less than the mounting element thickness.

In Example 23, the subject matter of any one or more of Examples 14-22 optionally include wherein the augment is a flange augment.

In Example 24, the subject matter of any one or more of Examples 14-23 optionally include wherein the contourable portion is a first extension contourable portion, the augment further comprising a second extension contourable portion, and wherein the first extension contourable portion and the second extension contourable portion are spaced apart and joined to one another by a contourable crossmember.

In Example 25, the subject matter of any one or more of Examples 14-24 optionally include the body further comprising: a first extension extending away from the first end portion in a first direction; a second extension extending away from the first end portion in a second direction; a contourable crossmember extending from the first extension to the second extension; and a third extension disposed between the first extension and the second extension, the third extension having a third extension contourable portion.

In Example 26, the subject matter of any one or more of Examples 14-25 optionally include wherein the first surface comprises a smooth surface, and wherein the second surface comprises a porous material that promotes boney ingrowth.

In Example 27, the subject matter of any one or more of Examples 14-26 optionally include wherein a contourable portion marker is provided on the contourable portion to indicate a location on the body that is adapted to be bent and contoured to the bone of the patient.

Example 28 is a method of semi-customizing an acetabular shell to a bone of a patient, the method comprising: assessing the patient for an acetabular bone defect and identifying a type of acetabular bone defect; selecting a type of an augment based on the type of the acetabular bone defect identified in the patient, the augment having: a body having a first surface and a second surface opposite the first surface, the body extending from a first end portion to a second end portion, wherein the first end portion is adapted to be fixed to the acetabular shell, the body further including a contourable portion and a mounting element, wherein the contourable portion has a contourable portion thickness defined between the first surface and the second surface, wherein the mounting element has a mounting element thickness defined between the first surface and the second surface, and wherein the contourable portion thickness is less than the mounting element thickness; and bending the contourable portion of the body to approximate a contour of the bone of the patient.

In Example 29, the subject matter of Example 28 optionally includes securing the augment to the acetabular shell; orienting the augment at the bone; securing the acetabular shell to the bone; and securing the augment to the bone at the mounting element.

In Example 30, the subject matter of any one or more of Examples 28-29 optionally include wherein bending the contourable portion comprises, bending the contourable portion at a contourable portion marker that indicates a location on the body that is adapted to be bent to conform to the bone of the patient.

In Example 31, the subject matter of any one or more of Examples 28-30 optionally include wherein the contourable portion is a region between the first end portion and the mounting element.

In Example 32, the subject matter of any one or more of Examples 28-31 optionally include wherein the contourable portion is a region between the mounting element and a second mounting element.

In Example 33, the subject matter of any one or more of Examples 28-32 optionally include wherein the contourable portion has a contourable portion thickness defined between the first surface and the second surface, wherein the mounting element has a mounting element thickness defined between the first surface and the second surface, and wherein the contourable portion thickness is less than the mounting element thickness.

In Example 34, the subject matter of any one or more of Examples 28-33 optionally include wherein orienting the augment at the bone includes orienting the augment at a superior position on an ilium of the bone.

In Example 35, the subject matter of any one or more of Examples 28-34 optionally include wherein orienting the augment at the bone includes orienting the augment at an inferior position on an ischium or ramus of the bone.

In Example 36, the subject matter of any one or more of Examples 28-35 optionally include wherein securing the augment to the acetabular shell comprises moving a first portion of a locking mechanism on the first end portion of the augment relative to a second portion of the locking mechanism that includes a recess in the acetabular shell.

In Example 37, the subject matter of Example 36 optionally includes wherein moving the first portion of the locking mechanism relative to the second portion of the locking mechanism comprises moving a pawl of the locking mechanism relative to teeth of the locking mechanism.

In Example 38, the subject matter of any one or more of Examples 36-37 optionally include wherein moving the first portion of the locking mechanism relative to the second portion of the locking mechanism includes inserting a wedge between the first and second portions of the locking mechanism.

In Example 39, the subject matter of any one or more of Examples 36-38 optionally include wherein moving the first portion of the locking mechanism relative to the second portion of the locking mechanism includes driving expandable fingers of the first portion into a locked state.

In Example 40, the subject matter of any one or more of Examples 36-39 optionally include wherein moving the first portion of the locking mechanism relative to the second portion of the locking mechanism includes screwing a tapered screw to drive expandable fingers of the first portion of the locking mechanism into a locked state.

What is claimed is:

1. An acetabular shell and augment system for attachment to a bone, the system comprising:
    an augment extending from a first end portion to a second end portion and having a first surface and a second surface opposite the first surface, the first end portion including a first portion of a locking mechanism having a pawl, the augment including at least a first mounting element adapted to be fixed to the bone and at least a first contourable portion positioned between the first end portion and the first mounting element; and
    a shell extending from a rim to an apex, the shell having first thickness defined between a first shell surface and a second shell surface, the shell including a second portion of the locking mechanism, wherein the second portion of the locking mechanism includes a recess that extends into the first shell surface from the rim towards the apex, and wherein the second portion of the locking mechanism includes radially extending teeth located in the recess, and wherein the first portion of the locking mechanism and the second portion of the locking mechanism are adapted to move relative to one another in a direction from the rim towards the apex to cause a change in state from an unlocked state to a locked state to engage the pawl with the teeth and thereby fixedly couple the augment to the shell, wherein the first contourable portion is adapted to allow the first mounting element to move relative to the first end portion when the locking mechanism is in the locked state.

2. The system of claim 1, wherein the recess formed in the shell is sized and shaped to receive the first end portion of the augment.

3. The system of claim 1, wherein the first end portion comprises a portion of a ratchet-style locking mechanism.

4. The system of claim 1, the augment further comprising:
    a second mounting element, each of the first and second mounting elements having an opening extending through the augment from the first surface to the second surface, wherein each of the first and second mounting elements are adapted to be fixed to the bone; and
    a second contourable portion located between the first and second mounting elements, wherein the second contourable portion has a contourable portion thickness defined between the first surface and the second surface, wherein the first mounting element has a first mounting element thickness defined between the first surface and the second surface, and wherein the second mounting element has a second mounting element thickness between the first surface and the second surface, and wherein the second contourable portion thickness is less than the first mounting element thickness and is less than the second mounting element thickness.

5. The system of claim 1, wherein
    the first mounting element has an opening extending through the augment from the first surface to the second surface, wherein the first mounting element is adapted to be fixed to the bone, and wherein
    the first contourable portion is more bendable than the first mounting element.

6. The system of claim 5, further comprising a second mounting element having a second opening extending through the augment from the first surface to the second surface, wherein a second contourable portion is located between the first mounting element and the second mounting element.

7. The system of claim 1, wherein the augment includes a plurality of mounting elements including the first mounting element and a plurality of contourable portions including the first contourable portion, wherein the augment further includes a plurality of cutouts extending through the augment from the first surface to the second surface.

8. The system of claim 7, wherein the plurality of cutouts are defined by at least a portion of the plurality of mounting elements.

9. The system of claim 7, wherein at least one contourable portion of the plurality of contourable portions extends from the first mounting element of the plurality of mounting elements to a second mounting element of the plurality of mounting elements.

10. A method for securing an augment to an acetabular shell, the method comprising:
    receiving an augment having a first surface and a second surface opposite the first surface, the augment extending from a first end portion to a second end portion, the first end portion including a first portion of a locking mechanism having a pawl, the augment including at least a first mounting element adapted to be fixed to the bone and at least a first contourable portion positioned between the first end portion and the first mounting element;

receiving an acetabular shell extending from a rim to an apex, the shell having a first thickness defined between a first shell surface and a second shell surface, the shell including a second portion of the locking mechanism, wherein the second portion of the locking mechanism includes a recess that extends into the first shell surface from the rim towards the apex, and wherein the second portion of the locking mechanism includes radially extending teeth located in the recess; and moving the first portion of the locking mechanism relative to the second portion of the locking mechanism in a direction from the rim towards the apex to cause to engage and fixedly couple the first portion of the locking mechanism and the second portion of the locking mechanism into a locked state by engaging the pawl with the teeth and thereby fixedly coupling the augment to the shell, wherein the first contourable portion is adapted to allow the first mounting element to move relative to the first end portion when the locking mechanism is in the locked state.

11. The method of claim 10, wherein moving the first portion of the locking mechanism relative to the second portion of the locking mechanism includes inserting the first portion of the locking mechanism into the recess of the second portion of the locking mechanism.

12. An acetabular shell and augment system for attachment to a bone, the system comprising:

an augment extending from a first end portion to a second end portion and having a first surface and a second surface opposite the first surface, the first end portion including a first portion of a locking mechanism, wherein a proximal end surface of the first end portion includes a plurality of pawls, the augment further comprising:

a first mounting element and a second mounting element, each of the first and second mounting elements having an opening extending through the augment from the first surface to the second surface, wherein each of the first and second mounting elements are adapted to be fixed to the bone; and a contourable portion located between the first and second mounting elements, wherein the contourable portion has a contourable portion thickness defined between the first surface and the second surface, wherein the first mounting element has a first mounting element thickness defined between the first surface and the second surface, and wherein the second mounting element has a second mounting element thickness between the first surface and the second surface and wherein the contourable portion thickness is less than the first mounting element thickness and is less than the second mounting element thickness; and a shell extending from a rim to an apex portion, the shell having a first thickness defined between a first shell surface forming an exterior of the shell and a second shell surface forming an interior of the shell, the shell including a second portion of the locking mechanism, wherein the second portion of the locking mechanism includes a recess disposed between the first shell surface and the second shell surface, the recess including a first recess opening that extends through the first shell surface towards the second shell surface and a second recess opening that extends through the rim towards the apex portion, wherein the second portion of the locking mechanism includes a plurality of teeth located at an inner surface of the recess and extending radially away from the inner surface of the recess towards the first shell surface, and wherein the first portion of the locking mechanism and the second portion of the locking mechanism are adapted to move relative to one another in a direction from the rim towards the apex portion to automatically cause a change in state from an unlocked state to a locked state by engaging at least a first pawl of the plurality of pawls with a first tooth of the plurality of teeth, and by engaging at least a second pawl of the plurality of pawls with a second tooth of the plurality of teeth, thereby fixedly coupling the augment to the shell.

13. The system of claim 12, wherein the recess formed in the shell is sized and shaped to receive the first end portion of the augment.

14. The system of claim 12, wherein the recess comprises a cavity located in between the first shell surface and the second shell surface.

15. The system of claim 12, wherein the contourable portion is a first extension contourable portion, the augment further comprising:

a second extension contourable portion, and wherein the first extension contourable portion and the second extension contourable portion are spaced apart and joined to one another by a contourable crossmember.

* * * * *